(12) United States Patent
Romanov et al.

(10) Patent No.: US 11,073,628 B2
(45) Date of Patent: Jul. 27, 2021

(54) POSITRON EMISSION TOMOGRAPHY (PET) TIMING CALIBRATION USING COINCIDENCES INVOLVING HIGH-ENERGY CASCADE GAMMA FROM PROMPT-GAMMA POSITRON EMITTERS

(71) Applicant: KONINKLIJKE PHILIPS N.V., Eindhoven (NL)

(72) Inventors: Leonid Romanov, Mayfield Heights, OH (US); Andriy Andreyev, Willoughby Hills, OH (US); Thomas Christoher Bulgrin, Columbia Station, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 77 days.

(21) Appl. No.: 16/610,508

(22) PCT Filed: May 4, 2018

(86) PCT No.: PCT/EP2018/061566
§ 371 (c)(1),
(2) Date: Nov. 3, 2019

(87) PCT Pub. No.: WO2018/202878
PCT Pub. Date: Nov. 8, 2018

(65) Prior Publication Data
US 2021/0157020 A1    May 27, 2021

Related U.S. Application Data (60) Provisional application No. 62/501,384, filed on May 4, 2017.

(51) Int. Cl.
*G01T 7/00* (2006.01)
*A61B 6/00* (2006.01)
(Continued)

(52) U.S. Cl.
CPC .............. *G01T 7/005* (2013.01); *A61B 6/037* (2013.01); *A61B 6/585* (2013.01); *G01T 1/172* (2013.01); *G01T 1/2985* (2013.01); *G06T 11/005* (2013.01)

(58) Field of Classification Search
CPC ....... G01T 1/172; G01T 1/2985; G01T 7/005; G06T 11/005; A61B 6/037; A61B 6/585
See application file for complete search history.

(56) References Cited

U.S. PATENT DOCUMENTS 9,069,089 B2    6/2015  Olcott
2008/0265167 A1  10/2008  Laurence
(Continued)

FOREIGN PATENT DOCUMENTS

CN    106108934 A    11/2016
WO    2016046703 A2   3/2016

OTHER PUBLICATIONS

International Search Report and Written Opinion of PCT/EP2018/061566, dated Jul. 9, 2018.
(Continued)

*Primary Examiner* — Michael C Bryant (57) ABSTRACT

Timing calibration of a positron emission tomography (PET) imaging device (2) uses a radioactive source (20) comprising a positron-emitting radioisotope having a decay path including emission of two oppositely directed 511 keV gamma rays and a cascade gamma ray at a cascade gamma ray energy. A timestamped radiation detection event data set acquired from the radioactive source by the PET imaging device is processed using energy window filtering (32) and time window filtering (36) to generate a coincidence data set (40, 42, 44) including event pairs (40) each consisting of two coincident 511 keV events and cascade event pairs (42) or triplets (44) each consisting of at least one coincident 511 keV event and a coincident cascade event at the cascade gamma ray energy. A timing calibration (12) is generated using the coincidence data set. The timing calibration comprises offset times for PET detectors of the PET imaging device.

20 Claims, 4 Drawing Sheets

(51) Int. Cl.
  *A61B 6/03* (2006.01)
  *G01T 1/29* (2006.01)
  *G06T 11/00* (2006.01)
  *G01T 1/172* (2006.01)

(56) References Cited

U.S. PATENT DOCUMENTS

2010/0040197 A1* 2/2010 Maniawski ............ A61B 6/037
   378/65
2014/0217294 A1 8/2014 Rothfuss
2015/0185339 A1 7/2015 Lage
2016/0131774 A1 5/2016 Lage

OTHER PUBLICATIONS

Moses, et al "Timing Calibration in PET using a Time Alignment Probe", IEEE Transaction on Nuclear Science, vol. 53, No. 5, pp. 2660-2665, 2006.
Andreyev, A. et al "Feasibility Study of Dual Isotope PET" Nuclear Science Symposium Conference Record, pp. 2108-2111, 2010.
Lage, Eduardo "Recovery and Normalization of Triple Coincidences in PET", Medical Physics, vol. 42, No. 3, pp. 1398-1410, 2015.

* cited by examiner

POSITRON EMISSION TOMOGRAPHY (PET) TIMING CALIBRATION USING COINCIDENCES INVOLVING HIGH-ENERGY CASCADE GAMMA FROM PROMPT-GAMMA POSITRON EMITTERS

CROSS-REFERENCE TO PRIOR APPLICATIONS

This application is the U.S. National Phase application under 35 U.S.C. § 371 of International Application No. PCT/EP2018/061566, filed on May 4, 2018, which claims the benefit of U.S. Provisional Patent Application No. 62/501,384, filed on May 4, 2017. These applications are hereby incorporated by reference herein.

FIELD

The following relates generally to the medical imaging arts, positron emission tomography (PET) imaging arts, PET imaging device calibration arts, and related arts.

BACKGROUND

In positron emission tomography (PET) imaging, a positron-emitting radiopharmaceutical is administered to a patient, e.g. by intravascular infusion. Each emitted positron annihilates with an electron thereby generating two oppositely directed 511 keV gamma rays. One or more rings of PET detectors arranged around the examination region detect radiation emitted from the patient. Each detected event is timestamped. An energy window is applied to select the 511 keV events, and a coincidence detection time window is applied to detect coincident pairs of such 511 keV events that occur within the time window. Each such coincident pair defines a line of response (LOR) connecting the two detection events at the PET detectors. The sourcing positron is thus localized to having been emitted at some point along the LOR.

In time-of-flight (TOF) PET, the time stamps of the two 511 keV events of a coincident pair are further used to localize the positron emission along the LOR. For example, if the two 511 keV events are precisely coincident then this TOF localization places the positron emission at the midpoint of the LOR, equidistant from the two detection events. On the other hand, if the two events have some time difference $\Delta t$, then the magnitude and sign of this difference (i.e. which detection occurred first) enables the positron emission to be localized along the LOR a quantitative distance closer to the first detection event and further from the second detection event, leveraging the knowledge that the two emitted gamma rays each travel at the speed of light. TOF PET can provide improved sensitivity and ultimately improved reconstructed images by leveraging this additional event localization along the LOR.

TOF localization requires fast radiation detectors. For example, a PET imaging device sized to receive and image a human being may have a PET detector ring with a diameter of approximately 70 cm. Consider a positron emitted at a location that is 20 cm away from the closer detector and 50 cm away from the further detector. The transit time for the gamma ray to the first detector is $t_1 = 20 \text{ cm}/3.00 \times 10^{10}$ cm/s which is 667 ps. The transit time for the gamma ray to the second detector is $t_2 = 50 \text{ cm}/3.00 \times 10^{10}$ cm/s which 1667 ps. Thus, the time-of-flight difference is $\Delta t = t_2 - t_1 = 1000$ ps. For an event closer to the center of the bore this time difference is smaller, e.g. for the first event at 30 cm from the closer detector and the second event at 40 cm from the further detector, $\Delta t = 333$ ps. Thus, the detector speed must be sufficient to measure time differences on the order of a few tens to a few hundreds of picoseconds, depending on the desired time-of-flight resolution.

In practice, the different detectors of the PET detector rings may have various time delays, which in turn result in the time stamps for two events which are truly simultaneous having systematically different non-zero coincidence time offset. To ensure good temporal resolution, it is advantageous for the time stamps output by the PET detectors to be calibrated for such relative time lags between different PET detectors.

The following discloses a new and improved systems and methods.

SUMMARY

In one disclosed aspect, a timing calibration device is disclosed for performing timing calibration of a positron emission tomography (PET) imaging device. The timing calibration device comprises: a radioactive source comprising a positron-emitting radioisotope having a decay path including emission of two oppositely directed 511 keV gamma rays and at least one cascade gamma ray at a cascade gamma ray energy different from 511 keV; an electronic processor operatively connected to receive a timestamped radiation detection event data set acquired from the radioactive source by the PET imaging device; and a non-transitory storage medium storing instructions readable and executable by the electronic processor to perform a timing calibration method. The method includes processing the timestamped radiation detection event data set using energy window filtering and time window filtering to generate a coincidence data set including coincident gammas (or counts) each consisting of two coincident 511 keV gammas, or one 511 keV gamma and one coincident cascade event at the cascade gamma ray energy; and generating a timing calibration for the PET imaging device comprising offset times for PET detectors of the PET imaging device using the coincidence data set.

In another disclosed aspect, a non-transitory storage medium stores instructions readable and executable by an electronic processor to perform a timing calibration method operating on a timestamped radiation detection event data set acquired by a PET imaging device for a stationary radioactive point source comprising a positron-emitting radioisotope. The timing calibration method comprises: performing energy filtering of the timestamped radiation detection event data set to generate an energy-filtered radiation detection event data set consisting of 511 keV events and cascade events at a cascade gamma ray energy of the positron-emitting radioisotope; performing time window filtering of the energy-filtered radiation detection event data set to generate a coincidence data set including event pairs each consisting of two coincident 511 keV events and cascade event pairs or triplets each consisting of at least one coincident 511 keV event and a coincident cascade event; and generating a timing calibration for the PET imaging device comprising offset times for PET detectors of the PET imaging device using the coincidence data set.

In another disclosed aspect, a timing calibration method is disclosed for a positron emission tomography (PET) imaging device. Using the PET imaging device, a timestamped radiation detection event data set is acquired for a radioactive source comprising a positron-emitting radioisotope having a decay path including emission of two oppositely directed 511 keV gamma rays and at least one cascade gamma ray at a cascade gamma ray energy different from 511 keV. Using an electronic processor, this data set is energy window filtered and time window filtered to generate a coincidence data set including (i) event pairs each consisting of two coincident 511 keV events and (ii) cascade event pairs or triplets each consisting of at least one coincident 511 keV event and a coincident cascade event at the cascade gamma ray energy. Using the electronic processor, a timing calibration is generated for the PET imaging device by simultaneously solving a set of equations relating signed differences between timestamps of the event pairs and timestamps of the cascade event pairs or triplets to offset times for the PET detectors of the PET imaging device. The timing calibration comprises the solved offset times for PET detectors of the PET imaging device.

One advantage resides in providing for timing calibration of positron emission tomography (PET) detectors used in conventional or time-of-flight (TOF) PET imaging which can be performed using a single compact radioactive source that closely approximates a point source.

Another advantage resides in providing such timing calibration using the single compact radioactive source with the source kept stationary throughout the calibration data collection process.

Another advantage resides in providing for timing calibration of PET detectors used in TOF PET imaging without the need for multiple, or distributed or movable radioactive sources.

Another advantage resides in one or more of the foregoing advantages using a conventional radioactive source that may also be used for other types of calibration such as detector sensitivity calibration.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
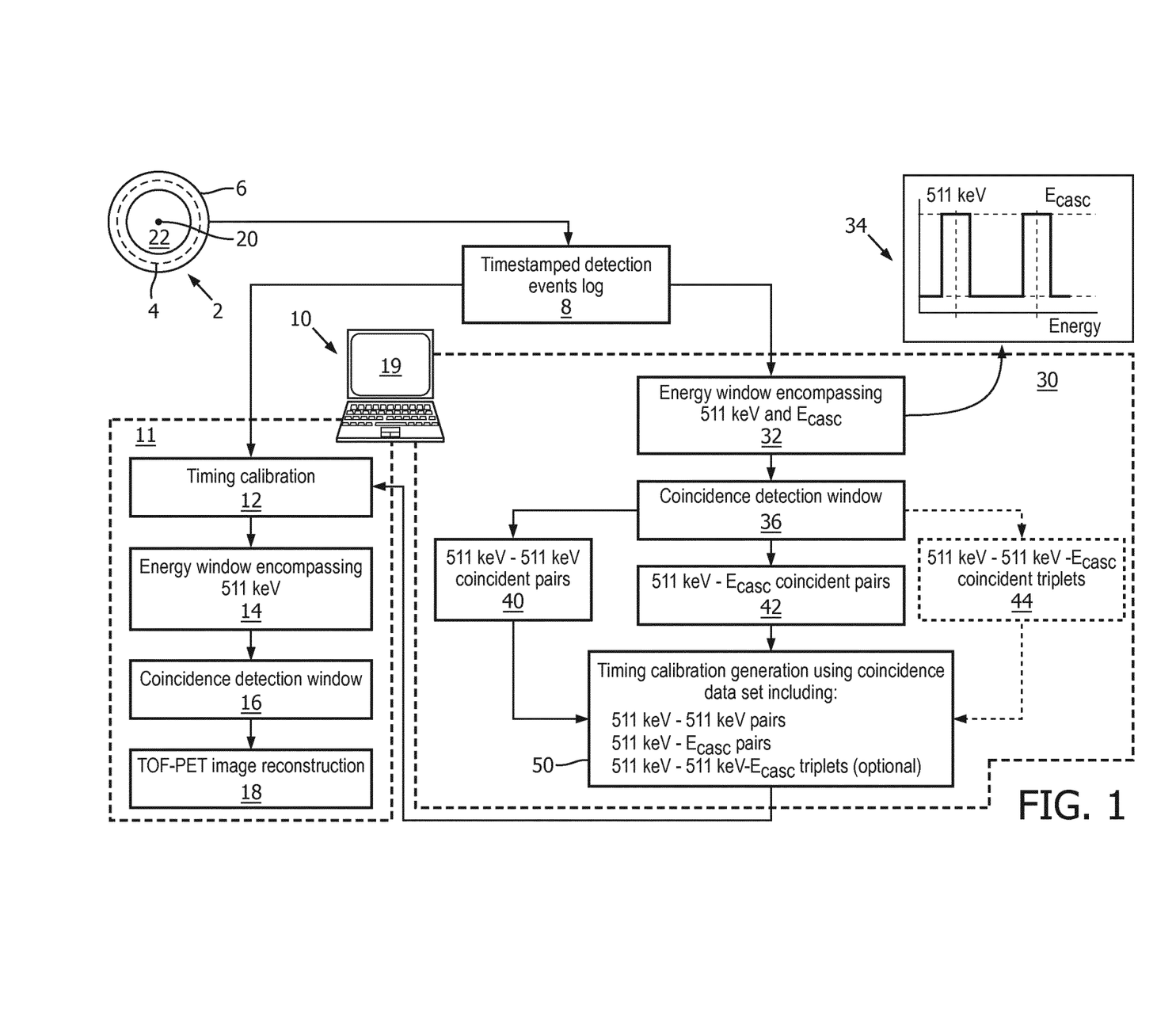
FIG. 1 diagrammatically illustrates a positron emission tomography (PET) imaging device with time-of-flight (TOF) imaging capability, and including a detector timing calibration as disclosed herein.

With reference to FIG. 1, an illustrative positron emission tomography (PET) imaging device 2 includes a PET detector ring 4 disposed in an annular gantry or housing 6. FIG. 1 diagrammatically depicts the PET imaging device 2 viewed from the end, i.e. viewed along the axis of the PET detector ring 4. The PET imaging device 2 may be stand-alone, or may be part of a hybrid imaging system such as a combined PET/transmission computed tomography (CT) imaging device which includes both the illustrated PET modality and a CT imaging modality (not shown) including a rotating gantry supporting a transmission x-ray source and opposing x-ray detector. The PET imaging device 2 is controlled by an electronic imaging system controller (not shown, e.g. a microprocessor or microcontroller and associated electronics such as memory, clocking circuitry, connecting electrical wiring, and so forth, which may be variously embodied as a computer, dedicated PET controller hardware, various combinations thereof, or so forth) to acquire time-stamped radioactive particle (e.g. gamma ray) detection events which are stored in a timestamped detection events log 8 (e.g., a non-transitory storage medium comprising a magnetic disk, electronic data storage, or so forth). By way of one non-limiting illustrative example, the illustrative PET imaging device 2 may be the PET modality of a Vereos™ Digital PET/CT scanner, available from Koninklijke Philips N.V., Eindhoven, the Netherlands.

As used herein, the term "PET detector" denotes an element of the PET detector ring 4 that detects a gamma ray or other radiation ray or particle. The division of the PET detector ring 4 into individual detectors is done annularly, i.e. around the circumference of the PET detector ring 4, and also optionally may be done axially, i.e. the PET detector ring 4 may comprise multiple rings of PET detectors. Each PET detector may be variously referred to in the art, e.g. as a PET detector pixel, PET detector element, or so forth, and may be variously constructed, e.g. employing a scintillator coupled with photomultiplier tubes (PMTs) with Anger logic employed to localize detection events, or as scintillator/silicon photomultiplier (SiPM) elements with one-to-one scintillator-SiPM correspondence, or so forth. Groups of PET detectors may be manufactured as PET detector modules, with the detectors of a given PET detector module sharing some common control and/or drive circuitry, which in some embodiments may include shared time stamping circuitry. Similarly, groups of PET detector modules may form PET detector tiles that again may share some common circuitry. As a consequence, it is sometimes the case for certain types of PET detector rings that a group of PET detectors (e.g. those of a single PET detector module or tile) may exhibit similar or even identical time offsets relative to the other PET detector modules or tiles of the modular and/or tiled PET detector ring.

An electronic processor 10 is programmed to perform various processing of timestamped detection events stored in the timestamped detection events log 8. The electronic processor 10 may take various forms, e.g. may be a desktop computer, server computer operatively connected with the PET imaging device 2 via a hospital data network or the like (e.g. wired and/or wireless Ethernet, optionally including data link via the Internet), or so forth. The executed instructions are suitably stored on a non-transitory storage medium (not shown), e.g. a hard disk or other magnetic storage medium, and/or a FLASH memory or other electronic storage medium, and/or so forth. In some embodiments, the electronic processor 10 that performs the various events data processing described here also performs control functions for controlling the PET imaging device 2 to acquire the events data stored in the timestamped detection events log 8; alternatively these may be separate processors.

With continuing reference to FIG. 1, the electronic processor 10 performs PET image reconstruction 11 as follows. The timestamped events data stored in the events data log 8 serve as input imaging data to be reconstructed. To compensate for various time delays of the various PET detectors, a timing calibration 12 is applied to the time stamps generated by the detectors of the PET detector ring 6. In general, the timing calibration 12 stores, for each detector, a time offset which is applied to the time stamps of the detection events detected by that PET detector. These offsets are predetermined (i.e. calibrated) to compensate for the different time delays of the various PET detectors.

An energy window is applied in an operation 14 to select events with energy of 511 keV within some chosen energy resolution. This energy corresponds to the energy of the two oppositely directed gamma rays emitted by an electron-positron annihilation event. A coincidence detection window 16 is applied to the 511 keV events to detect coincident 511 keV events which are coincident within a chosen time window. This time window should be larger than the largest expected time-of-flight time difference $\Delta t$ so as to avoid filtering out true coincidences in which the individual gamma rays have a large TOF difference. For example, if the gantry 6 has a diameter of 70 cm then the largest credible $\Delta t$ is about 70 cm/3.00×10$^{10}$ cm/s or about 2330 ps, so the time window applied in the operation 14 should be larger than this.

The resulting 511 keV gamma ray event pairs are reconstructed to generate a reconstructed TOF-PET image in an operation 18. The reconstruction may employ any suitable image reconstruction algorithm, e.g. maximum likelihood-expectation maximization (MLEM), ordered subset expectation maximization (OSEM), or so forth, suitably employing a TOF kernel for TOF-PET reconstruction. Conceptually, each 511 keV gamma ray pair defines a positron emission along the LOR connecting the two events, and the TOF localization further localizes the positron along the LOR. The resulting image may be displayed on a display 19, printed as a hardcopy, and/or otherwise utilized.

The TOF PET reconstruction 11 employs the timing calibration 12 to correct for timestamp errors due to varying time lags amongst the detectors of the PET detector ring 4. For PET detector sensitivity calibration purposes and the like, point radioactive sources are known. FIG. 1 depicts such a point radioactive source 20 disposed in the examination region 22 of the PET imaging device 2. Such a point radiation source includes a radioisotope that emits positrons. For example, a National Electrical Manufacturers Association (NEMA) standard point source consists of a $^{22}$Na point source of diameter 0.25 mm embedded in an acrylic cube of 10 mm/side. When $^{22}$Na is used as radioactive component, no frequent refills are needed due to long half-life of this positron emitter. A radioactive source that is sufficiently compact to effectively approximate a point in space, e.g. the radioactive source has a maximum dimension of five millimeters or less in some embodiments, and more preferably is spherical and has a maximum diameter of 0.5 millimeters or less, e.g. as in the aforementioned NEMA standard point source, has certain advantages such as reducing the material cost for the radioactive material and simplifying the computational processing of the coincident events to determine the timing calibration. However, it is contemplated to employ a more spatially extended radioactive source for the timing calibration, e.g. a radioactive source having a maximum dimension of twenty millimeters or less in some embodiments. A calibration radioactive source of even larger size is contemplated, though accuracy of the timing calibration may be reduced if the radioactive source is too large. It should be noted that these non-limiting illustrative dimensions are for the radioactive material itself, while the host structure (e.g. the acrylic cube in the case of the aforementioned NEMA standard point source) may be larger to facilitate handling or manipulation of the source.

For calibration purposes, it is advantageous for the point radioactive source 20 to be equidistant from the two PET detectors of every pair of PET detectors of the PET imaging device that can define a line of response (LOR) passing through the point radiation source 20. For the illustrative PET imaging device 2 with the circular PET detector ring 4, this is achieved by centering the point radioactive source 20 in the center of the circular cross-section of the PET detector ring 4.

Figure 2:
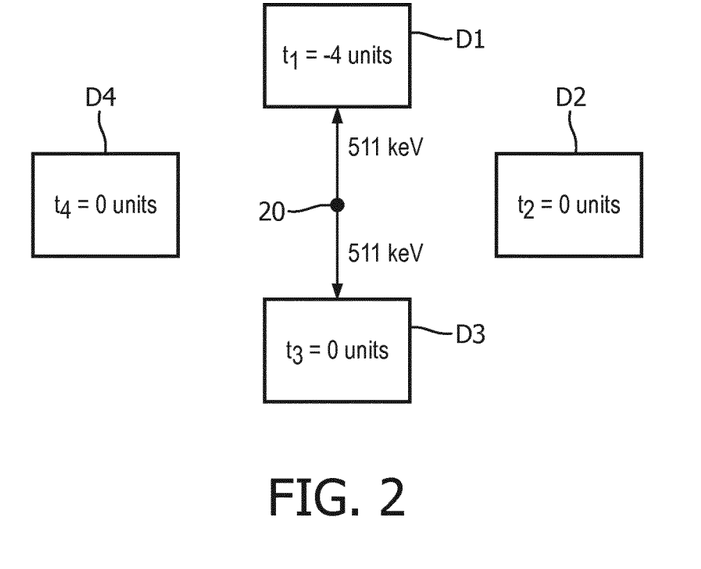
FIG. 2 diagrammatically illustrates a calibration datum consisting of a coincident 511 keV-511 keV gamma ray pair produced by a decay event emitting a positron, and acquired using two detectors, with one of the detectors having a timing offset relative to the other detectors of the PET ring.

FIG. 2 diagrammatically illustrates the point radioactive source 20 along with four illustrative PET detectors D1, D2, D3, D4 of the PET detector ring 4 of FIG. 1. (It will be appreciated that the PET detector ring 4 generally includes many more than four PET detectors, and that they are usually closely spaced around the circumference of the ring so as to detect 511 keV gamma rays at any angle). FIG. 2 also shows a coincident 511 keV event pair due to a positron-electron annihilation, i.e. two oppositely directed 511 keV gamma rays—one of which is detected by the PET detector D1, and the other of which is detected by the PET detector D3. In this illustrative example, it is further assumed that the actual time lag of the three detectors D2, D3, D4 is the same (arbitrarily designated zero) whereas the actual time lag of the detector D1 is four time units slower than these other three detectors. To correct this situation, the timing calibration should assign an offset time of −4 for PET detector D1 and an offset time of zero for the other three PET detectors D2, D3, D4, as indicated in FIG. 2. More generally, the PET detector offset for the n$^{th}$ PET detector is denoted herein as $t_n$. The goal of the timing calibration is thus to optimize the values of the offset times $\{t_n\}_{n=1, \ldots, N}$ for the PET detectors (where N is the number of PET detectors of the PET detector ring 4). With the point radioactive source 20 positioned equidistant from the two PET detectors of every pair of PET detectors of the PET imaging device that can define a LOR passing through the point radiation source 20, it follows that for each coincident 511 keV event pair (such as that shown in FIG. 2), an equation $\Delta t = t_i - t_j$ can be written, where i and j index the PET detectors acquiring the two coincident 511 keV events and $\Delta t$ is the signed time difference between the timestamps of the two coincident 511 keV events. (By "signed" it is meant that the time difference could be negative if $\Delta t$ is computed as the earlier timestamp minus the later timestamp; or positive if vice versa). By simultaneously solving all such equations, it is expected to optimize the values of the offset times $\{t_n\}_{n=1,\ldots,N}$ for the PET detectors.

However, using the single immovable radioactive point source 20 for timing calibration encounters a substantial problem. Because of the point nature of the point radioactive source 20 and the fact that each line-of-response (LOR) defined by a coincident 511 keV gamma ray pair is indeed a line, it follows that for a given PET detector all the LORs will connect with the same opposite PET detector along the line extending from the given PET detector through the point radioactive source 20. Thus, every LOR of PET detector D1 connects with opposite PET detector D3; and likewise, every LOR of PET detector D3 connects with opposite PET detector D1. Thus, offset times $t_1$ and $t_3$ for the respective PET detectors D1 D3 are determined only from coincident 511 keV detection event pairs involving PET detectors D1, D3. These pairs all have the equation $\Delta t = t_i - t_j$ written as $-4 = t_1 - t_3$.

Figure 3:
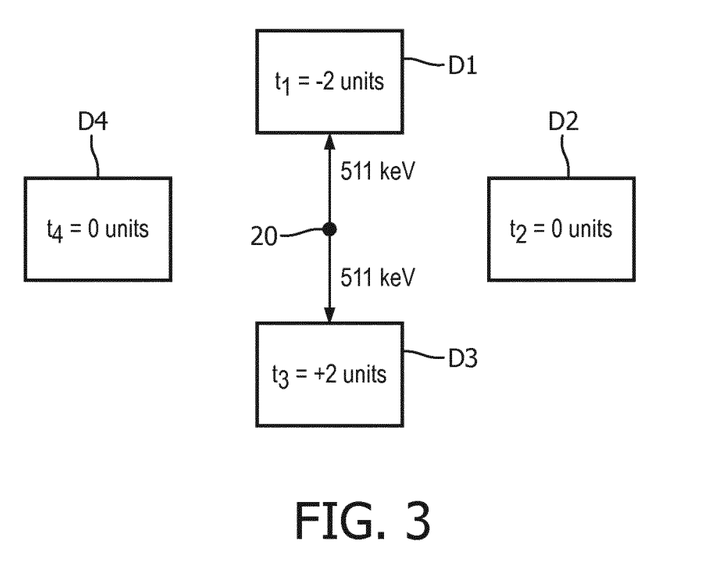
FIG. 3 diagrammatically illustrates the calibration datum of FIG. 2 can result in erroneous timing calibration of the involved PET detectors.

Now comparing FIG. 2 and FIG. 3, the equation $-4 = t_1 - t_3$ has no single solution. While the ground truth (i.e. correct) solution is depicted in FIG. 2, where $t_1 = -4$ and $t_3 = 0$, another possible (but erroneous) solution is depicted in FIG. 3, where $t_1 = -2$ and $t_3 = +2$. Both provide the time difference $\Delta t = -4$.

In sum, if the centered and stationary point radioactive source 20 is used for timing calibration, then for any given detector element i there will be exactly one opposing detector element j through which all LORs involving detector element i pass. While the difference between the offset times of detectors i and j can therefore be determined, there is no way to apportion that difference between the two PET detectors i and j.

To resolve this problem, a spatially distributed calibration radioactive source might be used, rather than a point radioactive source. In this way, the LORs associated with detector element i will encompass more than one other opposing PET detector, and the resulting set of equations involving PET detector i may become solvable. But if the calibration radioactive source is too large, the uncertainty in the location of the positron-electron annihilation events along the LORs becomes large, thereby reducing accuracy of the timing calibration. Conversely, if the spatially distributed radioactive source is made too small (while still being larger than a point source) then the LORs involving PET detector i will all involve a small group of adjacent opposing PET detectors. If this small group resides entirely on a single PET detector module, then the offset times for all detectors of the small group may be similar (e.g. if the time lags are principally due to a delay in a transmission line commonly shared by all the detectors of the PET detector module). In this case the situation may be similar to that of FIG. 2, just with redundant data from additional similar opposing detectors.

Another option to resolve the problem presented with reference to FIG. 2 is to employ a plurality of point radioactive sources, or to move a single point radioactive source during the data acquisition. Because the sources (or the moving source) are still point sources, the issues of spatial uncertainty are mitigated. However, using multiple point radioactive sources increases cost and requires mounting hardware to position each source at a different location in the examination region. Moving a single point radioactive source during the acquisition is mechanically complex and difficult to implement, and again requires complex mounting hardware. Moreover, using either multiple point sources or a single moving point source removes the geometric simplicity of a single stationary centrally located point radioactive source which is equidistant from the two PET detectors of every pair of PET detectors of the PET imaging device that can define a LOR passing through the point radiation source 20. This complicates the evaluation of the resulting matrix employed in the simultaneous solution of the resulting equations. To see this, consider that the equation $\Delta t = t_i - t_j$ relies upon the two PET detectors i and j being equidistant from the point source. If instead the point radioactive source is not at the center of the PET detector ring 4 then there will be a constant term that is the equation becomes $\Delta t = t_i - t_j + T_{ij}$ where the term $T_{ij}$ accounts for the actual time-of-flight difference from the point source to respective detectors i and j due to the different flight distances. Moreover, $T_{ij}$ is generally different for each pair of detectors and depends on the specific geometry of the detector ring and the placement of the point radiation source.

Disclosed herein is an alternative solution which enables the use of a single stationary point radioactive source positioned at the isocenter of the PET detector ring 4, that is, at the position equidistant from the two PET detectors of every pair of PET detectors of the PET detector ring 4 that can define a LOR passing through the point radiation source 20. The disclosed approaches are premised on the observation that some positron-emitting radioisotopes decay by emission of two oppositely directed 511 keV gamma rays (produced by positron-electron annihilation) and a cascade gamma ray at a cascade gamma ray energy different from 511 keV. More generally, the cascade gamma ray energy is denoted as $E_{casc}$. The emitted two oppositely directed 511 keV gamma rays are conventionally used for PET imaging. However, during the image processing 11, the third gamma ray, namely the cascade gamma ray, is removed by the energy filtering operation 14 (see FIG. 1) which retains only gamma rays within a relatively narrow passband around 511 keV. The timing calibration approaches disclosed herein are further premised on the further observation that the cascade gamma ray is not directed in any preferential direction.

An example of such a positron-emitting radioisotope is $^{22}$Na, which has a decay path including emission of two oppositely directed 511 keV gamma rays (produced by positron-electron annihilation) and a cascade gamma ray at an energy of about 1275 keV (that is, $E_{casc}$=1275 keV), which is not constrained to any particular direction of emission as compared with the directions of the two oppositely directed 511 keV gamma rays. The cascade gamma ray at 1275 keV is emitted about 90% of the time due to de-excitation of the neon atom generated from the $^{22}$Na isotope by the positron emission. The delay between the positron emission and the cascade gamma ray emission is about 3 picoseconds.

In the illustrative embodiments, the point radioactive source 20 is assumed to be a $^{22}$Na point radioactive source is a NEMA-standard point source comprising a $^{22}$Na point source of diameter 0.25 mm embedded in an acrylic cube of 10 mm/side. However, other point source sizes can be employed. Furthermore, while a $^{22}$Na point source is employed herein as the illustrative point radioactive source, the disclosed approaches may employ any positron-emitting radioisotope that also emits a statistically useful fraction of cascade gamma rays at an energy other than 511 keV. It is preferable that the energy of the cascade gamma to be several energy resolution sigmas larger than the 511 keV, in order for it to be distinguishable despite the finite detector energy resolution and Compton scattering. Some other contemplated radioisotopes include K-38, Cu-60, etc, however, the shorter half-life of these isotopes makes them less convenient to use as timing calibration source on a daily basis.

Figure 4:
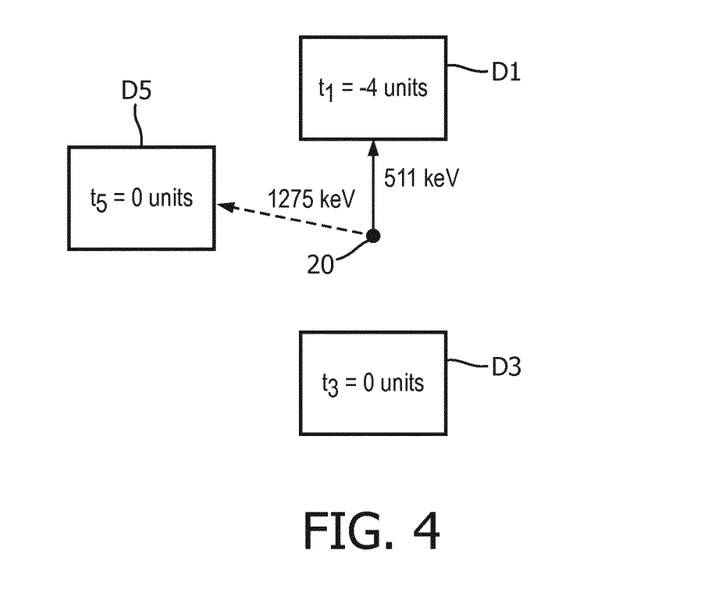
FIG. 4 diagrammatically illustrates a calibration datum consisting of a coincident 511 keV-1275 keV gamma ray pair produced by a decay event, and acquired using two detectors in which one detector has a timing offset.
Figure 5:
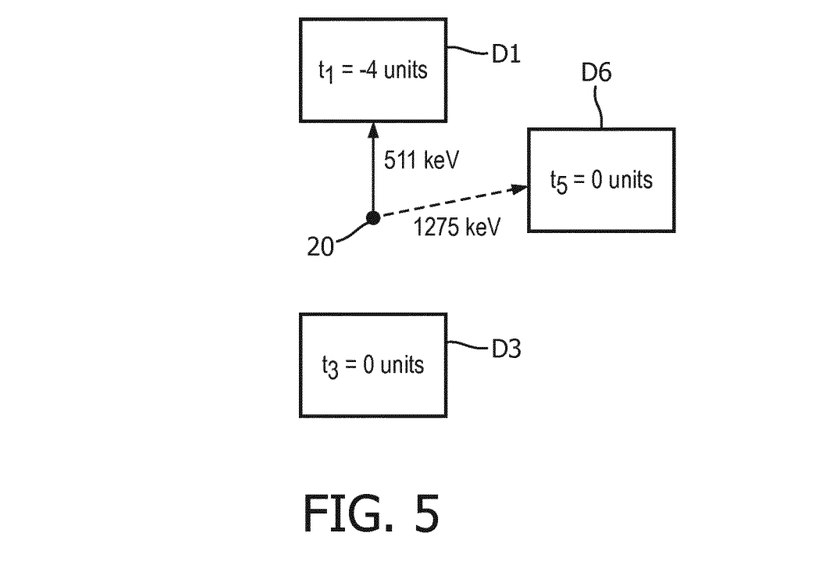
FIG. 5 diagrammatically illustrates a calibration datum consisting of a coincident 511 keV-1275 keV gamma ray pair analogous to that of FIG. 4 but with the cascade gamma ray at 1275 keV emitted in a different direction and detected by a different detector.

With reference now to FIGS. 4 and 5, the disclosed timing calibration approach leveraging cascade gamma rays emitted by the point radioactive source is illustrated. The detector configuration shown in FIG. 2 is again considered, with the detector D1 again having an offset time of −4 and the detector D3 again having an offset time of zero. As shown in FIG. 4, it is assumed here that one of the two 511 keV gamma rays is lost due to scattering away from the detector ring, absorption, or some other loss mechanism; while a third gamma ray, namely the cascade gamma ray having energy 1275 keV, is also emitted following the positron emission, due to de-excitation of the Ne atom to its ground state. (Note, the neon atom is produced by transmutation of the $^{22}$Na atom due to emission of the positron). As previously noted, the width of the coincidence detection window 16 should be larger than the largest expected time-of-flight time difference $\Delta t$, which is on the order of 2330 ps for a typical body-sized medical imaging PET gantry having a diameter of around 70 cm. Thus, the average 3 ps delay between the positron emission and the subsequent cascade gamma ray emission in Na-22 as well as the time needed for positron to annihilate should not affect the measured timing centroid offset much with respect to the coincidence detection 16. As recognized herein, for the purpose of timing calibration the cascade gamma ray has a substantial advantage: it is not directionally correlated with the two oppositely directed 511 keV gamma rays. Thus, while every LOR involving detector D1 defined by a 511 keV-511 keV gamma ray pair necessarily (in the absence of scattering) also involves detector D3, such constraint in no way applies to the cascade gamma ray at 1275 keV, which may be detected by any PET detector of the PET detector ring 4. By way of non-limiting illustration, FIG. 4 arbitrarily depicts the cascade gamma ray at 1275 keV being detected by some PET detector D5. However, as depicted in FIG. 5, the next event involving the detector D1 may have the cascade gamma ray at 1275 keV being detected by a different PET detector D6, and so on.

Figure 6:
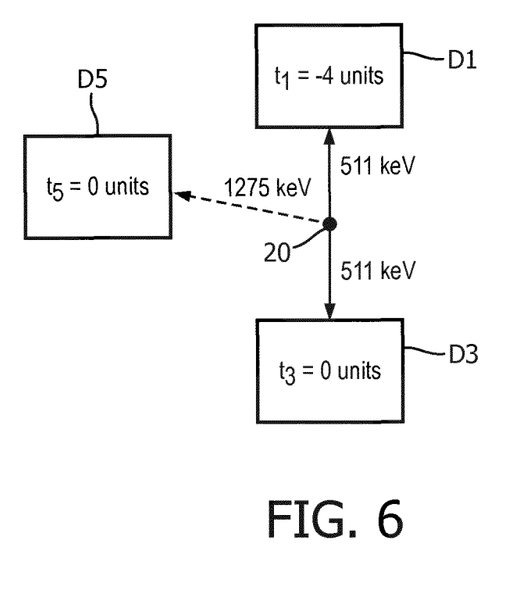
FIG. 6 diagrammatically illustrates another calibration datum consisting of a coincident 511 keV-511 keV-1275 keV gamma ray triplet produced by a decay event emitting a positron, and acquired using three detectors in which one detector has a timing offset. The coincident 511 keV-511 keV-1275 keV gamma ray triplet may alternatively be viewed as three coincident pairs: a 511 keV-511 keV pair and two 511 keV-1275 keV pairs that may originate from a single radioactive decay of Na-22 or from three separate decays.

With reference to FIG. 6, it is also possible to detect all three coincident gamma rays emitted by a $^{22}$Na decay event which emits a cascade gamma ray. The three coincident gamma rays are: the two oppositely directed 511 keV gamma rays, and the cascade gamma ray $E_{casc}$=1275 keV. The coincidence triplet depicted in FIG. 6 can also be interpreted as one double coincidence of 511-511 keV and two cascade gamma coincidences of 511-1275 keV.

With returning reference to FIG. 1, a timing calibration method 30 is shown which leveraged the foregoing observations, and in particular leverages the additional cascade gamma rays to enable use of the single stationary point radioactive source 20 for performing the timing calibration. An energy window is applied in an operation 32 to select both (1) events with energy of 511 keV and (2) events at a cascade gamma ray energy different from 511 keV (e.g. at 1275 keV in the $^{22}$Na radioisotope example). The operation 32 may, for example, employ a selection function 34 having a double passband with a first passband centered at 511 keV and a second passband centered at the cascade gamma ray energy (1275 keV in the $^{22}$Na example). Advantageously, this typically does not require any modification to the PET detector ring 4 or associated electronics; rather, it is performed on the event data stored in the timestamped detection events logs 8. In a variant contemplated embodiment, the selection function may have a single passband that is broad enough to encompass both 511 keV and 1275 keV. In any case the, energy acceptance window targeted at cascade gamma is preferably wide enough in order to also detect the scattered (either in the source or in the detectors) cascade gammas that will be detected at partial energy (e.g., 800 or 900 keV). In one implementation, if the regular upper energy threshold for 511 keV gammas is set to 640 keV, than any other gamma hits with energies detected above this threshold can be attributed to 1275 keV cascade gammas.

In an operation 36, a coincidence detection window is applied. The coincidence detection operation 36 is analogous to the coincidence detection operation 16 employed in the imaging processing 11, except that the operation 36 also captures coincidences that also involve cascade gammas. More particularly, the coincident 511 keV-511 keV pairs 40 are collected as in the operation 16—but the operation 36 also collects coincident 511 keV-1275 keV counts 42 (or, in the generalized case, collects coincident 511 keV-$E_{casc}$ counts 42). We further refer to such events as X-counts in the text (and with brief further reference to FIG. 4). In the example of FIG. 4, only one 511 keV gamma ray is detected, which is coincident with a cascade gamma ray. Such a situation may arise, for example, if a decay produces a triplet including two oppositely directed 511 keV gamma rays and a 1275 keV cascade gamma ray (e.g. as in FIG. 6); but one of the two oppositely directed 511 keV gamma rays is scattered or penetrated through the detector without interaction, or if the missing 511 keV gamma ray is oriented in a direction such that it is not detected by any PET detector of the PET detector ring 4.

With continuing reference to FIG. 1, in some embodiments the coincidence detection operation 36 also captures coincident 511 keV-511 keV-1275 keV triplets 44 (or, in the generalized case, collects coincident 511 keV-511 keV-$E_{casc}$ triplets 44) such as the example shown in FIG. 6. Alternatively, such a triplet can be processed as three coincident pairs: one coincident 511 keV-511 keV pair 40, and two coincident 511 keV-$E_{casc}$ pairs 42. This latter approach can simplify processing as existing timing calibration approaches that operate on coincident 511 keV-511 keV pairs can be readily adapted to additionally process the 511 keV-$E_{casc}$ pairs, and in some embodiments the same coincidence detection window 16 used to process imaging data may be used as the coincidence detection window 36. In this latter approach, the processing of coincident triplets 44 stored as triplets is suitably omitted (as indicated by showing this additional data set 44 using dotted lines in FIG. 1).

With further reference to FIG. 6, note that coincidences between detectors D1-D5, D1-D3 and D3-D5 need not to come as a part of single radioactive decay, but may occur as an ensemble of three separate decays. Note that in FIG. 6, the true coincidences between detectors D3 and D5 when using an immovable point source are only possible when using 511-Ecasc coincidences.

With continuing reference to FIG. 1, the detected coincident pairs 40, 42 and the (optional) detected coincident triplets 44 are inputs to a timing calibration generation operation 50, which generates and solves a set of equations based on these coincident pairs 40, 42 and (optional) triplets 44. The operation 50 entails simultaneously solving a set of equations for the values of the offset times $\{t_n\}_{n=1,\ldots,N}$ for the PET detectors (where again N is the number of PET detectors and $t_n$ is the offset time for the $n^{th}$ PET detector). The set of equations includes the following.

First, each 511 keV-511 keV event pair 40 is formulated by the operation 50 into the equation:

$$\Delta t = t_i - t_j \quad (1)$$

where i and j index the PET detectors acquiring the two coincident 511 keV events and Δt is the signed time difference between the timestamps of the two coincident 511 keV events.

If detected by the coincidence detector 36, each cascade event pair 42 is formulated by the operation 50 into the equation:

$$\Delta t = t_i - t_k \quad (2)$$

where i indexes the PET detector acquiring the coincident 511 keV event, k indexes the PET detector acquiring the coincident cascade event, and Δt is the signed time difference between the timestamps of the coincident 511 keV and cascade events.

If detected by the coincidence detector 36, each cascade event triplet 44 is formulated by the operation 50 into the three equations:

$$\Delta t_{ij} = t_i - t_j$$

$$\Delta t_{ik} = t_i - t_k$$

$$\Delta t_{jk} = t_j - t_k \quad (3)$$

where i and j index the PET detectors acquiring the two coincident 511 keV events, k indexes the PET detector acquiring the coincident cascade event, $\Delta t_{ij}$ is the signed time difference between the timestamps of the coincident 511 keV events, $\Delta t_{ik}$ is the signed time difference between the timestamp of the coincident 511 keV event acquired by the PET detector indexed i and the timestamp of the coincident cascade event, and $\Delta t_{jk}$ is the signed time difference between the timestamp of the coincident 511 keV event acquired by the PET detector indexed j and the timestamp of the coincident cascade event.

The operation 50 simultaneously solves the set of equations generated by formulating the acquired pairs and (optional) triplets into appropriate Equations (1), (2), or (3), and this set of equations is simultaneously solved to optimize the offset times $\{t_n\}_{n=1, \ldots, N}$ for the PET detectors. Any type of least squares optimization or the like may be employed. One potential iterative equation for finding $\{t_n\}_{n=1, \ldots, N}$ is:

$$t_n^{k+1} = t_n^k + \frac{\sum_{j \in \{N_n\}} \Delta t_{nj} - t_n^k - t_j}{|M_n|} \quad (4)$$

where k is the iteration index, j is the detected counts index running over the set of all counts $\{M_n\}$ that connect to the current detector element n. It should be noted that simultaneously solving the set of equations generally is done by a least squares optimization or the like, where the solved offset times are not exact values but rather are optimized to minimize a loss function, objective function, or other optimization fit metric.

If the timing calibration process 30 is being run to update an existing instance of the timing calibration 12, then the current values of the offset times $\{t_n\}_{n=1, \ldots, N}$ may optionally be used as initial values for this optimization. The timing calibration process 30 is being run for the first time, or if it is desired to ensure the optimization is not biased by the current offset time values, then the offset times $\{t_n\}_{n=1, \ldots, N}$ may be initialized to all zero values, or to random deviations about zero, or so forth. The resulting optimized values of the offset times $\{t_n\}_{n=1, \ldots, N}$ are then loaded into memory as the new or updated timing calibration 12 to be used thereafter in computing time-of-flight (TOF) localization for LORs acquired for image reconstruction by the imaging process 11.

In all cases involving the cascade gamma ray, the PET detectors i and j are always opposite to each other, but the PET detector k which detects the cascade gamma ray can be any other PET detector of the PET detector ring 4. This absence of directional correlation for the cascade gamma ray allows for improved determination of timing offsets, while still using the single stationary point radioactive source 20 centrally positioned equidistant from the two PET detectors of every pair of PET detectors of the PET imaging device that can define a LOR passing through the point radiation source 20. There is no definable line of response (LOR) between the PET detector i and the PET detector k (or between the PET detector j and the PET detector k), but since the point radioactive source 20 is a point source and its position is known, the timing information from such coincidence should be sufficient for timing calibration.

The central location of the point radioactive source 20 is beneficial as it provides simplified geometry resulting in straightforward Equations (1)-(3) which model the coincidence data set 40, 42, 44 as emitted by the radioactive source 20 with the radioactive source stationary throughout the acquisition of the timestamped radiation detection event data set. However, it would alternatively be possible to locate the point radioactive source elsewhere in the examination region 22. In this case the Equations (1)-(3) would need to be replaced by equations of the form $\Delta t = t_i - t_j + T_{ij}$ where the term $T_{ij}$ accounts for the actual time-of-flight difference from the point source to respective detector elements i and j due to the different flight distances. As previously noted, these factors $T_{ij}$ would generally be different for each pair of detectors and would depend on the specific geometry of the detector ring and the (non-central) placement of the point radiation source.

Monte Carlo simulations were performed using GATE v5.0.1 to simulate a PET camera geometry similar to the Philips Ingenuity™ TF PET/CT scanner. The simulated point radioactive source was a $^{22}$Na source with 0.1 MBq activity placed in the center of the field of view (i.e. equidistant from the two PET detectors of every pair of PET detectors of the PET imaging device that can define a LOR passing through the point radiation source 20) and simulated for 10 sec. The simulation acquired singles in two energy windows, one of 440-664 keV for 511 keV coincidences and 664-2000 keV for high energy cascade gamma rays. The singles were than matched into coincidences either double 511-511 keV or X-coincidence ones 511-1275 keV over the timing coincidence window of 4.5 ns. The simulation of 100 kBq centered Na-22 point source over 10 seconds acquisition time showed the following statistics was acquired: double 511-511 keV coincidences: ~58863 counts (cps=counts per second) and X-coincidences (511-1275 keV) coincidences: ~11528 counts. It may be estimated that the acquisition time or calibration source activity would need to be increased only moderately (cumulatively about 5 times) in order to gain similar counting statistics with 511-1275 keV coincidences as with the regular 511 keV-511 keV coincidences. The approach employing all possible types of coincidences 40, 42, 44 (see FIG. 1) is expected to be most advantageous. Standard 511-511 keV PET coincidences would benefit the timing calibration due to higher statistics, and coincidences involving cascade gamma rays would resolve timing calibration issues such as in those described with reference to FIGS. 2 and 3. Another factor is that, as previously noted, the timing offsets of PET detectors may be correlated over larger groups, such as PET detector modules or tiles, therefore, less statistics is needed to properly estimate an offset. The coincidences involving cascade gamma rays may be used in this way to stabilize the numerical solution of the standard double coincidence method by grouping elements together, relying on the double coincidence information to determine the high frequency components of the solution and using the X-coincidences to correct for any low frequency errors in the solution.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A timing calibration device for performing timing calibration of a positron emission tomography (PET) imaging device, the timing calibration device comprising:
   a radioactive source comprising a positron-emitting radioisotope having a decay path including emission of two oppositely directed 511 keV gamma rays and at least one cascade gamma ray at a cascade gamma ray energy different from 511 keV;
   an electronic processor operatively connected to receive a timestamped radiation detection event data set acquired from the radioactive source by the PET imaging device; and
   a non-transitory storage medium storing instructions readable and executable by the electronic processor to perform a timing calibration method (30) including:
      processing the timestamped radiation detection event data set using energy window filtering and time window filtering to generate a coincidence data set including event pairs each consisting of two coincident 511 keV events and cascade event pairs or triplets each consisting of at least one coincident 511 keV event and a coincident cascade event at the cascade gamma ray energy; and
      generating a timing calibration for the PET imaging device comprising offset times for PET detectors of the PET imaging device using the coincidence data set.

2. The timing calibration device of claim 1 wherein:
   the radioactive source has a maximum dimension of twenty millimeters or less; and
   the generating of the timing calibration includes modeling the coincidence data set as emitted by the radioactive source with the radioactive source stationary throughout the acquisition of the timestamped radiation detection event data set.

3. The timing calibration device of claim 1 wherein the radioactive source is spherical and has a maximum diameter of 1 millimeters or less.

4. The timing calibration device of claim 3 wherein the generating of the timing calibration includes modeling the coincidence data set as emitted by a single stationary point radioactive source located equidistant from the two PET detectors of every pair of PET detectors of the PET imaging device that can define a line of response (LOR) passing through the point radiation source.

5. The timing calibration device of claim 4, wherein the generating of the timing calibration for the PET imaging device includes simultaneously solving a set of equations for the values of the offset times $\{t_n\}_{n=1,\ldots,N}$ for the PET detectors where N is the number of PET detectors and $t_n$ is the offset time for the $n^{th}$ PET detector, where the set of equations includes:
   for each event pair the equation $\Delta t = t_i - t_j$ where i and j index the PET detectors acquiring the two coincident 511 keV events and $\Delta t$ is the signed time difference between the timestamps of the two coincident 511 keV events;
   for each cascade event pair the equation $\Delta t = t_i - t_k$ where indexes the PET detector acquiring the coincident 511 keV event, k indexes the PET detector acquiring the coincident cascade event, and $\Delta t$ is the signed time difference between the timestamps of the coincident 511 keV and cascade events; and
   for each cascade event triplet the equations $\Delta t_{ij} = t_i - t_j$ and $\Delta t_{ik} = t_i - t_k$ and $\Delta t_{jk} = t_j - t_k$ where i and j index the PET detectors acquiring the two coincident 511 keV events, k indexes the PET detector acquiring the coincident cascade event $\Delta t_{ij}$ is the signed time difference between the timestamps of the coincident 511 keV events, $\Delta t_{ik}$ is the signed time difference between the timestamp of the coincident 511 keV event acquired by the PET detector indexed i and the timestamp of the coincident cascade event, and $\Delta t_{jk}$ is the signed time difference between the timestamp of the coincident 511 keV event acquired by the PET detector indexed j and the timestamp of the coincident cascade event.

6. The timing calibration device of claim 5 wherein the processing of the timestamped radiation detection event data set generates the coincidence data set including only event pairs each consisting of two coincident 511 keV events and cascade event pairs each consisting of one coincident 511 keV event and a coincident cascade event at the cascade gamma ray energy and not including any cascade event triplets.

7. The timing calibration device of claim 5 wherein the processing of the timestamped radiation detection event data set generates the coincidence data set including only event pairs each consisting of two coincident 511 keV events and cascade triplets each consisting of two coincident 511 keV events and a coincident cascade event at the cascade gamma ray energy and not including any cascade event pairs.

8. The timing calibration device of claim 1 wherein the generating of the timing calibration includes modeling the coincidence data set as emitted by a single stationary point radioactive source.

9. The timing calibration device of claim 1 wherein the radioactive source comprises the radioisotope $^{22}$Na.

10. A non-transitory storage medium storing instructions readable and executable by an electronic processor to perform a timing calibration method operating on a timestamped radiation detection event data set acquired by a positron emission tomography (PET) imaging device for a stationary radioactive source comprising a positron-emitting radioisotope, the timing calibration method comprising:
   performing energy filtering of the timestamped radiation detection event data set to generate an energy-filtered radiation detection event data set consisting of 511 keV events and cascade events at a cascade gamma ray energy of the positron-emitting radioisotope;
   performing time window filtering of the energy-filtered radiation detection event data set to generate a coincidence data set including event pairs each consisting of two coincident 511 keV events and cascade event pairs or triplets each consisting of at least one coincident 511 keV event and a coincident cascade event; and generating a timing calibration for the PET imaging device comprising offset times for PET detectors of the PET imaging device using the coincidence data set.

11. The non-transitory storage medium of claim 10 wherein the timestamped radiation detection event data set is acquired by the PET imaging device for said stationary radioactive source located equidistant from the two PET detectors of every pair of PET detectors of the PET imaging device that can define a line of response (LOR) passing through the radiation source.

12. The non-transitory storage medium of claim 11 wherein the generating of the timing calibration for the PET imaging device includes simultaneously solving a set of equations for the values of the offset times $\{t_n\}_{n=1,\ldots,N}$ for the PET detectors where N is the number of PET detectors and $t_n$ is the offset time for the $n^{th}$ PET detector, where the set of equations includes:

for each event pair the equation $\Delta t = t_i - t_j$ where i and j index the PET detectors acquiring the two coincident 511 keV events and $\Delta t$ is the signed time difference between the timestamps of the two coincident 511 keV events;

for each cascade event pair the equation $\Delta t = t_i - t_k$ where i indexes the PET detector acquiring the coincident 511 keV event, k indexes the PET detector acquiring the coincident cascade event, and $\Delta t$ is the signed time difference between the timestamps of the coincident 511 keV and cascade events; and for each cascade event triplet the equations $\Delta t_{ij} = t_i - t_j$ and $\Delta t_{ik} = t_i - t_k$ and $\Delta t_{jk} = t_j - t_k$ where i and j index the PET detectors acquiring the two coincident 511 keV events, k indexes the PET detector acquiring the coincident cascade event, $\Delta t_{ij}$ is the signed time difference between the timestamps of the coincident 511 keV events, $\Delta t_{ik}$ is the signed time difference between the timestamp of the coincident 511 keV event acquired by the PET detector indexed i and the timestamp of the coincident cascade event, and $\Delta t_{jk}$ is the signed time difference between the timestamp of the coincident 511 keV event acquired by the PET detector indexed j and the timestamp of the coincident cascade event.

13. The non-transitory storage medium of claim 11 wherein the coincidence data set does not include any cascade event triplets (44), and the generating of the timing calibration for the PET imaging device includes simultaneously solving a set of equations for the values of the offset times $\{t_n\}_{n=1,\ldots,N}$ for the PET detectors where N is the number of PET detectors and $t_n$ is the offset time for the $n^{th}$ PET detector, where the set of equations includes:

for each event pair the equation $\Delta t = t_i - t_j$ where i and j index the PET detectors acquiring the two coincident 511 keV events and $\Delta t$ is the signed time difference between the timestamps of the two coincident 511 keV events;

for each cascade event pair the equation at $\Delta t = t_i - t_k$ where i indexes the PET detector acquiring the coincident 511 keV event, k indexes the PET detector acquiring the coincident cascade event, and $\Delta t$ is the signed time difference between the timestamps of the coincident 511 keV and cascade events.

14. The non-transitory storage medium of claim 11 wherein the coincidence data set does not include any cascade event pairs, and the generating of the timing calibration for the PET imaging device includes simultaneously solving a set of equations for the values of the offset times $\{t_n\}_{n=1,\ldots,N}$ for the PET detectors where N is the number of PET detectors and $t_n$ is the offset time for the $n^{th}$ PET detector, where the set of equations includes:

for each event pair the equation $\Delta t = t_i - t_j$ where i and j index the PET detectors acquiring the two coincident 511 keV events and $\Delta t$ is the signed time difference between the timestamps of the two coincident 511 keV events; and for each cascade event triplet the equations $\Delta t_{ij} = t_i - t_j$ and $\Delta t_{ik} = t_i - t_k$ and $\Delta t_{jk} = t_j - t_k$ where i and j index the PET detectors acquiring the two coincident 511 keV events, k indexes the PET detector acquiring the coincident cascade event, $\Delta t_{ij}$ is the signed time difference between the timestamps of the coincident 511 keV events, $\Delta t_{ik}$ is the signed time difference between the timestamp of the coincident 511 keV event acquired by the PET detector indexed i and the timestamp of the coincident cascade event, and $\Delta t_{jk}$ is the signed time difference between the timestamp of the coincident 511 keV event acquired by the PET detector indexed j and the timestamp of the coincident cascade event.

15. A timing calibration method for a positron emission tomography (PET) imaging device, the timing calibration method comprising:

using the PET imaging device, acquiring a timestamped radiation detection event data set for a radioactive source comprising a positron-emitting radioisotope having a decay path including emission of two oppositely directed 511 keV gamma rays and at least one cascade gamma ray; and using an electronic processor, energy window filtering and time window filtering the timestamped radiation detection event data set to generate a coincidence data set including (i) event pairs each consisting of two coincident 511 keV events and (ii) cascade event pairs or triplets each consisting of at least one coincident 511 keV event and a coincident cascade event at the cascade gamma ray energy; and using the electronic processor, generating a timing calibration for the PET imaging device comprising offset times for PET detectors of the PET imaging device by simultaneously solving a set of equations relating signed differences between timestamps of the event pairs and timestamps of the cascade event pairs or triplets to offset times for the PET detectors of the PET imaging device.

16. The timing calibration method of claim 15 wherein the radioactive source is kept stationary at a single location for the duration of the acquiring of the timestamped radiation detection event data set.

17. The timing calibration method of claim 16 wherein said single location is equidistant from the two PET detectors of every pair of PET detectors of the PET imaging device that can define a line of response passing through the radiation source.

18. The timing calibration method of claim 15 wherein the radioactive source has a maximum dimension of five millimeters or less.

19. The timing calibration method of claim 15 wherein the radioactive source comprises the radioisotope $^{22}$Na.

20. The timing calibration method of claim 19 further comprising:

using the PET imaging device, acquiring a timestamped imaging data set for an imaging subject;

using the electronic processor, energy window filtering and time window filtering the timestamped imaging data set to generate a coincidence imaging data set including event pairs each consisting of two coincident 511 keV events;

correcting timestamps of the coincidence imaging data set using the timing calibration for the PET imaging device to generate a timing-corrected coincidence imaging data set; and reconstructing the timing-corrected coincidence imaging data set using a time-of-flight (TOF) PET image reconstruction process to generate a reconstructed TOF PET image.

* * * * *